ns">

(12) United States Patent
Abboud

(10) Patent No.: US 11,083,819 B2
(45) Date of Patent: Aug. 10, 2021

(54) JOINT SPACERS

(71) Applicant: Joseph A. Abboud, Bryn Mawr, PA (US)

(72) Inventor: Joseph A. Abboud, Bryn Mawr, PA (US)

(73) Assignee: Joseph A. Abboud, Bryn Mawr, PA (US)

( * ) Notice: Subject to any disclaimer, the term of this patent is extended or adjusted under 35 U.S.C. 154(b) by 0 days.

(21) Appl. No.: 17/181,514

(22) Filed: Feb. 22, 2021

(65) Prior Publication Data

US 2021/0178019 A1 Jun. 17, 2021

Related U.S. Application Data

(63) Continuation of application No. PCT/IB2020/051000, filed on Feb. 10, 2020.

(60) Provisional application No. 62/804,800, filed on Feb. 13, 2019.

(51) Int. Cl.
| | | |
|---|---|---|
| *A61B 17/56* | (2006.01) | |
| *A61F 2/40* | (2006.01) | |
| *A61L 27/36* | (2006.01) | |
| *A61F 2/30* | (2006.01) | |

(52) U.S. Cl.
CPC .......... *A61L 27/365* (2013.01); *A61B 17/562* (2013.01); *A61F 2/30721* (2013.01); *A61F 2/40* (2013.01); *A61L 27/3604* (2013.01); *A61L 27/3608* (2013.01); *A61L 27/3633* (2013.01); *A61F 2002/30153* (2013.01); *A61F 2002/30581* (2013.01); *A61F 2002/30754* (2013.01); *A61F 2002/4088* (2013.01); *A61L 2430/24* (2013.01)

(58) Field of Classification Search
CPC ...... A61F 2/40; A61F 2/44; A61F 2002/4615; A61F 2002/30574; A61L 27/365; A61L 27/3604; A61L 27/3633; A61B 17/562
See application file for complete search history.

(56) References Cited

U.S. PATENT DOCUMENTS

| | | |
|---|---|---|
| 5,545,221 A | 8/1996 | Hang-Fu |
| 6,656,488 B2 | 12/2003 | Yi et al. |
| 8,480,647 B2 | 7/2013 | Shohat et al. |

(Continued)

FOREIGN PATENT DOCUMENTS

| | | |
|---|---|---|
| WO | 99/18886 A1 | 4/1999 |
| WO | 2013/068466 A1 | 5/2013 |

(Continued)

OTHER PUBLICATIONS

International Search Report and Written Opinion of the International Searching Authority dated Apr. 23, 2020 in International Application No. PCT/IB2020/051000.

(Continued)

*Primary Examiner* — Brian A Dukert
(74) *Attorney, Agent, or Firm* — Sughrue Mion, PLLC

(57) ABSTRACT

A joint spacer is provided for treatment of a joint of a human subject, the joint spacer including a pouch having a wall including a dermal graft material. The joint spacer is configured to be inserted into a space of the joint, and is shaped, when the pouch is inserted into the space and filled, to provide mechanical support to the joint. Other embodiments are also described.

18 Claims, 3 Drawing Sheets

(56) References Cited

U.S. PATENT DOCUMENTS

| | | | |
|---|---|---|---|
| 8,894,713 B2 * | 11/2014 | Shohat | A61F 2/4081 |
| | | | 623/19.13 |
| 9,289,307 B2 | 3/2016 | Shohat | |
| 9,314,944 B2 | 4/2016 | Shohat et al. | |
| 9,770,337 B2 * | 9/2017 | Shohat | A61B 17/562 |
| 2009/0198332 A1 | 8/2009 | Becker | |
| 2014/0074245 A1 | 3/2014 | Shohat et al. | |
| 2016/0256286 A1 | 9/2016 | Morris et al. | |
| 2018/0028326 A1 | 2/2018 | Vanleeuwen et al. | |

FOREIGN PATENT DOCUMENTS

| | | |
|---|---|---|
| WO | 2019/025982 A1 | 2/2019 |
| WO | 2019/171181 A2 | 9/2019 |

OTHER PUBLICATIONS

Annaidh AN et al., "Characterising the Anisotropic Mechanical Properties of Excised Human Skin," School of Mechanical & Materials Engineering, University College Dublin (2012) (23 pages total).
ArthroFLEX® product brochure (2011) (4 pages total).
Gallagher AJ et al., "Dynamic Tensile Properties of Human Skin," IRCOBI Conference (2012), pp. 494-502 (9 pages total).

* cited by examiner

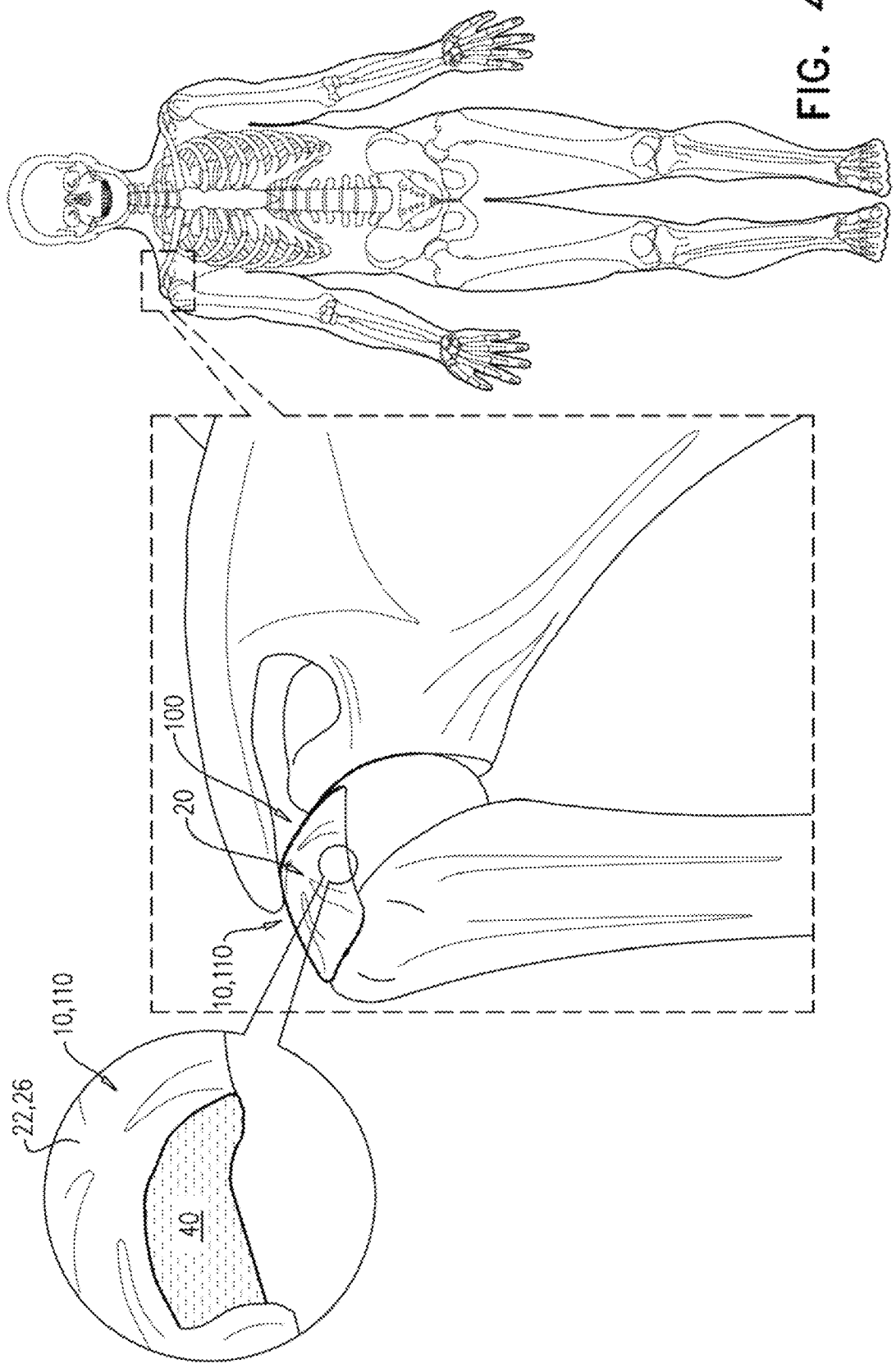

JOINT SPACERS

CROSS-REFERENCE TO RELATED APPLICATIONS

The present application is a continuation of International Appl. No. PCT/IB2020/051000, filed Feb. 10, 2020, which published as PCT Publication WO 2020/165716, and which claims priority from U.S. Provisional Application 62/804,800, filed Feb. 13, 2019. All of the above-mentioned applications are incorporated herein by reference.

FIELD OF THE APPLICATION

The present invention relates generally to techniques for treating joints, and specifically to joint spacers.

BACKGROUND OF THE APPLICATION

Common shoulder injuries include subacromial bursitis, tendinitis, and tendon tears, such as of the rotator cuff tendons. Subacromial bursitis is characterized by inflammation and swelling of the bursa between the rotator cuff and the acromion.

U.S. Pat. No. 8,753,390 to Shohat describes a prosthesis for reducing injury to soft tissues of the body, including an implantable member adapted to simulate at least one of a size or a shape of a naturally occurring bursa, where the member may be inflatable or otherwise expandable, flexible or rigid, and may be composed of a biocompatible, biodegradable, or non-biodegradable material. The member is adapted to be implanted at a musculoskeletal attachment site or at a site between a muscle and a bone, and is shaped and sized to reduce injury to the site. The prosthesis may also include a plug which seals the prosthesis automatically upon removal of an inflation tube.

US Patent Application Publication 2016/0256286 to Morris et al. describes a tissue positioning device including a biocompatible member having a size and shape suitable for placement within a space adjacent to a tissue to be positioned and which acts to maintain the tissue in a desired position. The member may be a rigid or flexible spacer having a defined shape, or a bladder capable of receiving and being at least partially expanded by a filler material. The device can made from a variety of materials or a composite of materials as needed, and may include one or more attachment means by which it can be secured to nearby tissues such that it is maintained in a desired spatial location. The filler material can be any of a number of substances, including liquids, gases, a curable liquid such as bone cement or urethane foam, or a spring.

US Patent Application Publication 2007/0078477 to Heneveld et al. describes an anatomical spacer which includes a bladder expandable from a deflated position to an inflated position. A membrane extends between opposing surfaces of the bladder, and an inflation port is placed in communication with the bladder. The inflation port is configured to receive inflation media to fill the bladder from the deflated position to the inflated position. A method is also provided to deploy the spacer into an anatomical location from a cannula.

SUMMARY OF THE APPLICATION

In embodiments of the present invention, a joint spacer is provided for treatment of a joint of a human subject. The joint spacer comprises a pouch having a wall. The joint spacer is configured to be inserted into a space of the joint, and is shaped, when the pouch is inserted into the space and filled, to provide mechanical support to the joint. For some applications, the joint spacer may simulate at the size or shape of a natural bursa. For some applications, the joint spacer is a subacromial spacer and the joint is a shoulder joint, and the subacromial spacer is shaped and sized so as to be insertable into a subacromial space of the shoulder joint to provide support to the shoulder joint.

For some applications, the wall of the pouch comprises a dermal graft material. Implanted dermal graft material is generally stable for many months or years, which enables the joint spacer to provide long-term treatment to the joint. In addition, dermal graft material has been used for many years as an implant material, and is thus known to be safe for long-term implantation.

For some applications, the joint spacer comprises a volume of adipose tissue suitable for filling the pouch. The joint spacer is configured to be inserted into the space of the joint, and is shaped, when the pouch is inserted into the space and filled with the volume of the adipose tissue, to provide mechanical support to the joint. For some of these applications, the adipose tissue comprises autologous adipose tissue obtained from the subject, using techniques known in the art for obtaining autologous adipose tissue.

For some applications, the pouch, when filled to a greatest volume possible without plastic deformation of the wall, is shaped so as to define two major surfaces facing away from each other. For some applications, when the pouch is filled to the greatest volume possible without plastic deformation of the wall, each of the major surfaces bulges away from a plane between the two major surfaces. Alternatively or additionally, for some applications, when the pouch is filled to the greatest volume possible without plastic deformation of the wall, the two major surfaces are generally symmetrical about the plane between the two major surfaces. For example, the pouch may be generally sachet-shaped.

There is therefore provided, in accordance with an application of the present invention, apparatus including a joint spacer for treatment of a joint of a human subject, the joint spacer including:

a pouch having a wall including a dermal graft material, wherein the joint spacer is configured to be inserted into a space of the joint, and is shaped, when the pouch is inserted into the space and filled, to provide mechanical support to the joint.

For some applications, the joint spacer includes a filling port for the pouch.

For some applications, the pouch is configured, when the filling port is sealed and the pouch is filled to a greatest volume possible without plastic deformation of the wall, to remain intact upon application of a force, by squeezing the pouch between two rigid planar surfaces larger than the pouch, of 400 N.

For some applications, the pouch is configured, when the filling port is sealed and the pouch is filled to the greatest volume possible without plastic deformation of the wall, to not remain intact upon application of an external force, by squeezing the pouch between two rigid planar surfaces larger than the pouch, of 1200 N.

For some applications, the wall of the pouch does not include any metal or polymer.

For some applications, the wall of the pouch includes only biological material.

For some applications, an average thickness of the wall is between 1 and 4 mm.

For some applications, the pouch, when filled to a greatest volume possible without plastic deformation of the wall, is shaped so as to define two major surfaces facing away from each other, and each of the major surfaces bulges away from a plane between the two major surfaces.

For some applications, when the pouch is filled to the greatest volume possible without plastic deformation of the wall, the two major surfaces are generally symmetrical about the plane between the two major surfaces.

For some applications, the pouch, at least when not filled, is shaped so as to define two major surfaces facing away from each other, the major surfaces having respective generally rectangular perimeters.

For some applications, a ratio of the longer sides to the shorter sides of the generally rectangular perimeter of each of the major surfaces is between 1.25:1 and 1.75:1.

For some applications, the longer sides of the generally rectangular perimeter of each of the major surfaces have a length of between 2.5 and 7.5 cm.

For some applications, the pouch, when filled to a greatest volume possible without plastic deformation of the wall, has a volume of between 15 and 40 cc.

For some applications, the joint spacer is a subacromial spacer and the joint is a shoulder joint, and the subacromial spacer is shaped and sized so as to be insertable into a subacromial space of the shoulder joint to provide support to the shoulder joint.

For some applications, the apparatus further includes a volume of adipose tissue suitable for filling the pouch, and the joint spacer is shaped, when the pouch is filled with the volume of the adipose tissue, to provide the mechanical support to the joint.

There is further provided, in accordance with an application of the present invention, a method for treating a joint of a human subject, the method including:

inserting, into a space of the joint, a joint spacer including a pouch having a wall including a dermal graft material; and filling the pouch within the joint, such that the joint spacer provides mechanical support to the joint.

For some applications, the wall of the pouch does not include any metal or polymer.

For some applications, the pouch, when filled, is shaped so as to define two major surfaces facing away from each other, and each of the major surfaces bulges away from a plane between the two major surfaces.

For some applications, when the pouch is filled, the two major surfaces are generally symmetrical about the plane between the two major surfaces.

For some applications, the pouch, at least when not filled, is shaped so as to define two major surfaces facing away from each other, the major surfaces having respective generally rectangular perimeters.

For some applications, a ratio of the longer sides to the shorter sides of the generally rectangular perimeter of each of the major surfaces is between 1.25:1 and 1.75:1.

For some applications, the longer sides of the generally rectangular perimeter of each of the major surfaces have a length of between 2.5 and 7.5 cm.

For some applications, filling the pouch includes filling the pouch until the pouch has a volume of between 15 and 40 cc.

For some applications, an average thickness of the wall is between 1 and 4 mm.

For some applications, the joint spacer is a subacromial spacer and the joint is a shoulder joint, and inserting the joint spacer includes inserting the subacromial spacer into the space of the shoulder joint.

For some applications, filling the pouch includes filling the pouch with a volume of adipose tissue within the joint, such that the joint spacer provides the mechanical support to the joint.

There is still further provided, in accordance with an application of the present invention, apparatus including a joint spacer for treatment of a joint of a human subject, the joint spacer including:

a pouch; and a volume of adipose tissue suitable for filling the pouch, wherein the joint spacer is configured to be inserted into a space of the joint, and is shaped, when the pouch is inserted into the space and filled with the volume of the adipose tissue, to provide mechanical support to the joint.

For some applications, the joint spacer includes a filling port for the pouch.

For some applications, the pouch is configured, when the filling port is sealed and the pouch is filled to a greatest volume possible without plastic deformation of a wall of the pouch, to remain intact upon application of a force, by squeezing the pouch between two rigid planar surfaces larger than the pouch, of 400 N.

For some applications, the pouch is configured, when the filling port is sealed and the pouch is filled to the greatest volume possible without plastic deformation of the wall, to not remain intact upon application of an external force, by squeezing the pouch between two rigid planar surfaces larger than the pouch, of 1200 N.

For some applications, the pouch, when filled to a greatest volume possible without plastic deformation of a wall of the pouch, is shaped so as to define two major surfaces facing away from each other, and each of the major surfaces bulges away from a plane between the two major surfaces.

For some applications, when the pouch is filled to the greatest volume possible without plastic deformation of the wall, the two major surfaces are generally symmetrical about the plane between the two major surfaces.

For some applications, the pouch, at least when not filled, is shaped so as to define two major surfaces facing away from each other, the major surfaces having respective generally rectangular perimeters.

For some applications, a ratio of the longer sides to the shorter sides of the generally rectangular perimeter of each of the major surfaces is between 1.25:1 and 1.75:1.

For some applications, the longer sides of the generally rectangular perimeter of each of the major surfaces have a length of between 2.5 and 7.5 cm.

For some applications, the pouch, when filled to a greatest volume possible without plastic deformation of a wall of the pouch, has a volume of between 15 and 40 cc.

For some applications, the volume of the adipose tissue is between 15 and 40 cc.

For some applications, the joint spacer is a subacromial spacer and the joint is a shoulder joint, and the subacromial spacer is shaped and sized so as to be insertable into a subacromial space of the shoulder joint to provide support to the shoulder joint.

For some applications, the pouch has a wall including a dermal graft material.

There is additionally provided, in accordance with an application of the present invention, a method for treating a joint of a human subject, the method including:

inserting a joint spacer into a space of the joint; and filling a pouch of the joint spacer with a volume of adipose tissue within the joint, such that the joint spacer provides mechanical support to the joint.

For some applications, the adipose tissue includes autologous adipose tissue obtained from the subject.

For some applications, the pouch, when filled, is shaped so as to define two major surfaces facing away from each other, and each of the major surfaces bulges away from a plane between the two major surfaces.

For some applications, when the pouch is filled, the two major surfaces are generally symmetrical about the plane between the two major surfaces.

For some applications, the pouch, at least when not filled, is shaped so as to define two major surfaces facing away from each other, the major surfaces having respective generally rectangular perimeters.

For some applications, a ratio of the longer sides to the shorter sides of the generally rectangular perimeter of each of the major surfaces is between 1.25:1 and 1.75:1.

For some applications, the longer sides of the generally rectangular perimeter of each of the major surfaces have a length of between 2.5 and 7.5 cm.

For some applications, filling a pouch with the volume of the adipose tissue includes filling the pouch with between 15 and 40 cc of the adipose tissue.

For some applications, the joint spacer is a subacromial spacer and the joint is a shoulder joint, and inserting the joint spacer includes inserting the subacromial spacer into the space of the shoulder joint.

For some applications, the pouch has a wall including a dermal graft material.

The present invention will be more fully understood from the following detailed description of embodiments thereof, taken together with the drawings, in which:

BRIEF DESCRIPTION OF THE DRAWINGS

FIGS. 4A-B are schematic illustrations of a method of deploying the joint spacer of FIG. 1 into a subacromial space of a shoulder joint, in accordance with an application of the present invention.

DETAILED DESCRIPTION OF APPLICATIONS

Figure 1:
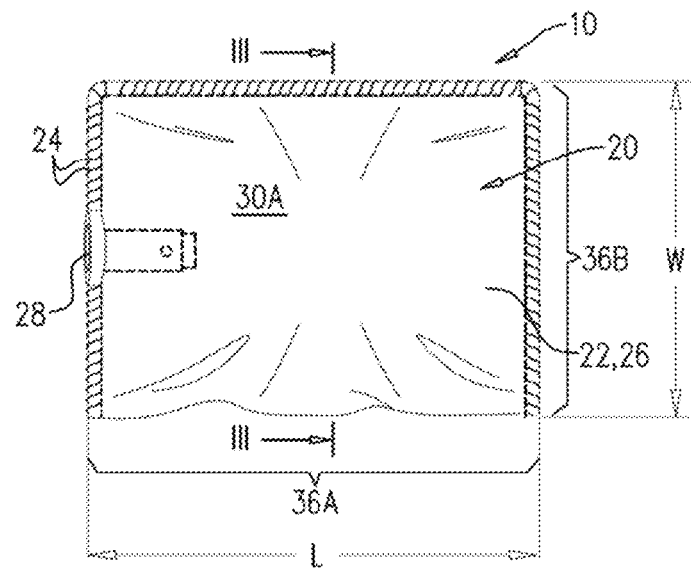
FIG. 1 is a schematic illustration of a joint spacer for treatment of a joint of a human subject, in accordance with an application of the present invention.

FIG. 1 is a schematic illustration of a joint spacer 10 for treatment of a joint of a human subject, in accordance with an application of the present invention. Joint spacer 10 comprises a pouch 20 having a wall 22. Joint spacer 10 is configured to be inserted into a space of the joint, and is shaped, when pouch 20 is inserted into the space and filled, to provide mechanical support to the joint, such as described hereinbelow with reference to FIGS. 4A-B. For some applications, joint spacer 10 may simulate at the size or shape of a natural bursa.

Pouch 20 is shaped so as to define a closed space therewithin. To this end, pouch 20 is sealed during production, such as by stitching (e.g., with one or more sutures 24), gluing, or annealing. For some applications, wall 22 is defined by two separate pieces of material that are sealed together, or by a single piece of material that is folded and sealed together on three sides.

For some applications, wall 22 is not shaped so as to define any openings that have a cross-sectional area greater than 0.5 mm2.

Typically, wall 22 is not blood-permeable.

For some applications, wall 22 comprises a dermal graft material 26. For example, dermal graft material 26 may comprise human skin.

For example, dermal graft material 26 may comprise ArthroFLEX® dermal allograft (Arthrex, Inc., Naples, Fla., USA), which is an acellular dermal extracellular matrix comprising allograft dermis that has been rendered acellular, without compromising biomechanical or biochemical properties. The rendering process causes the matrix to retain its growth factors, native collagen scaffold, and elastin, while removing donor DNA from the dermal matrix, ensuring a biocompatible scaffold.

Implanted dermal graft material 26 is generally stable for many months or years, which enables joint spacer 10 to provide long-term treatment to the joint. This long-term stability may in some cases be enhanced by neovascularization into dermal graft material 26. In addition, dermal graft material has been used for many years as an implant material, and is thus known to be safe for long-term implantation.

For some applications, joint spacer 10 comprises a filling port 28 for pouch 20. For example, filling port 28 may be self-sealing, e.g., similar to the self-sealing valve of a soccer ball. Alternatively, filling port 28 may not be self-sealing, e.g., may be shaped as a simple opening, and is sealed by the physician, for example using a suture gun or absorbable staple, or other closure techniques known in the surgical arts.

Typically, wall 22 of pouch 20 does not comprise any metal or polymer, and/or comprises only biological material. Dermal graft material 26 is typically strong enough to withstand the pressures applied to pouch 20 without additional structural support. Alternatively, wall 22 further comprises a non-dermal support structure, comprising, for example, metal or polymer, which may be, for example, interwoven into dermal graft material 26 and or shaped as one or more separate layers that are fixed to the dermal graft material.

For some applications, an average thickness of wall 22 is at least 1 mm, no more than 4 mm, and/or between 1 and 4 mm.

For some applications, pouch 20, when filled to a greatest volume possible without plastic deformation of wall 22, is shaped so as to define two major surfaces 30A and 30B facing away from each other. Major surfaces 30A and 30B have respective perimeters. (Dermal graft material 26 is typically somewhat elastic, and is typically, but not necessarily inflated to a level that causes some elastic expansion of pouch 20, while avoiding over-inflation to the point of irreversible plastic deformation.)

Figure 2:
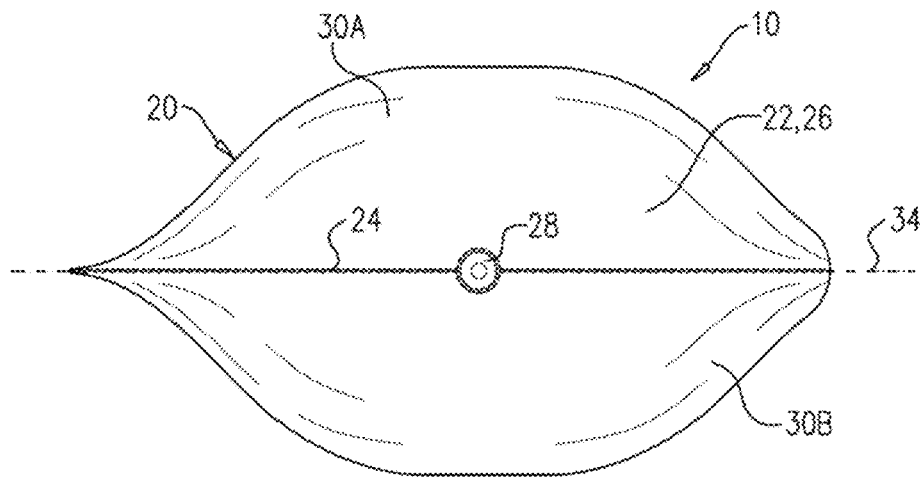
FIG. 2 is a schematic side-view of the joint spacer of FIG. 1, in accordance with an application of the present invention.
Figure 3:
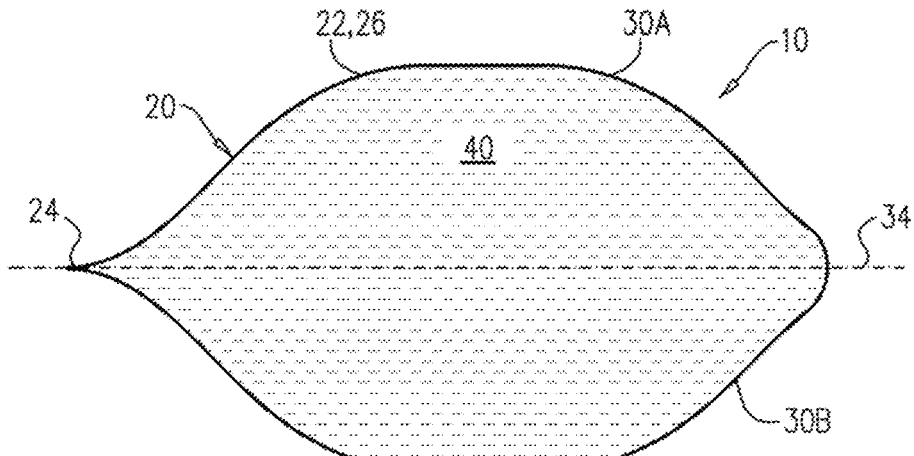
FIG. 3 is a schematic cross-sectional view of the joint spacer of FIG. 1 taken along line in accordance with an application of the present invention.

Reference is still made to FIG. 1, and is additionally made to FIGS. 2 and 3. FIG. 2 is a schematic sideview of joint spacer 10, in accordance with an application of the present invention. FIG. 3 is a schematic cross-sectional view of joint spacer 10 taken along line III-III of FIG. 1, in accordance with an application of the present invention.

For some applications, when pouch 20 is filled to a greatest volume possible without plastic deformation of wall 22, each of major surfaces 30A and 30B bulges away from a plane 34 between the two major surfaces. Alternatively or additionally, for some applications, when pouch 20 is filled to a greatest volume possible without plastic deformation of wall 22, the two major surfaces 30A and 30B are generally symmetrical about plane 34 between the two major surfaces. For example, pouch 20 may be generally sachet-shaped.

Further alternatively or additionally, for some applications, pouch 20, at least when not filled (and optionally also when filled), the respective perimeters of the two major surfaces 30A and 30B are generally rectangular, such as shown in the figures. For example, a ratio of longer sides 36A to shorter sides 36B of the generally rectangular perimeter of each of the major surfaces 30A and 30B may be between 1.25:1 and 1.75:1, such as between 1.4:1 and 1.6:1, e.g., 1.5:1. Alternatively (or optionally in combination with the above-mentioned ratios), longer sides 36A of the generally rectangular perimeter of each of the major surfaces 30A and 30B may have a length L of between 2.5 and 7.5 cm. Further alternatively (or optionally in combination with the above-mentioned ratios), shorter sides 36B of the generally rectangular perimeter of each of the major surfaces 30A and 30B may have a width W of between 1.6 and 5 cm.

For some applications, pouch 20 is provided in several different sizes, such as 3×2 cm (small), 5×3.5 cm (medium), and 6×4 cm (large). For example, a kit may be provided that includes at least one pouch 20 for each of the above-mentioned sizes.

For some applications, pouch 20, when filled to a greatest volume possible without plastic deformation of wall 22, has a volume of between 15 and 40 cc.

For some applications, joint spacer 10 is a subacromial spacer and the joint is a shoulder joint, and the subacromial spacer is shaped and sized so as to be insertable into a subacromial space of the shoulder joint to provide support to the shoulder joint, such as described hereinbelow with reference to FIGS. 4A-B. Alternatively, for example, the joint may be a knee or wrist joint, and joint spacer 10 may be shaped and sized so as to be insertable into the knee or wrist joint, respectively, to provide support to the knee or wrist joint, respectively.

Reference is still made to FIGS. 1-3. For some applications, joint spacer 10 comprises a volume of adipose tissue 40 suitable for filling pouch. In these applications, joint spacer 10 may or may not implement the features of joint spacer 10 described hereinabove. For example, wall 22 of pouch may or may not comprise dermal graft material 26. Joint spacer 10 is configured to be inserted into the space of the joint, and is shaped, when pouch 20 is inserted into the space and filled with the volume of adipose tissue 40, to provide mechanical support to the joint.

Alternatively, joint spacer 10 is filled with another material, such as saline solution, autologous blood, or bone marrow.

Figure 4A:
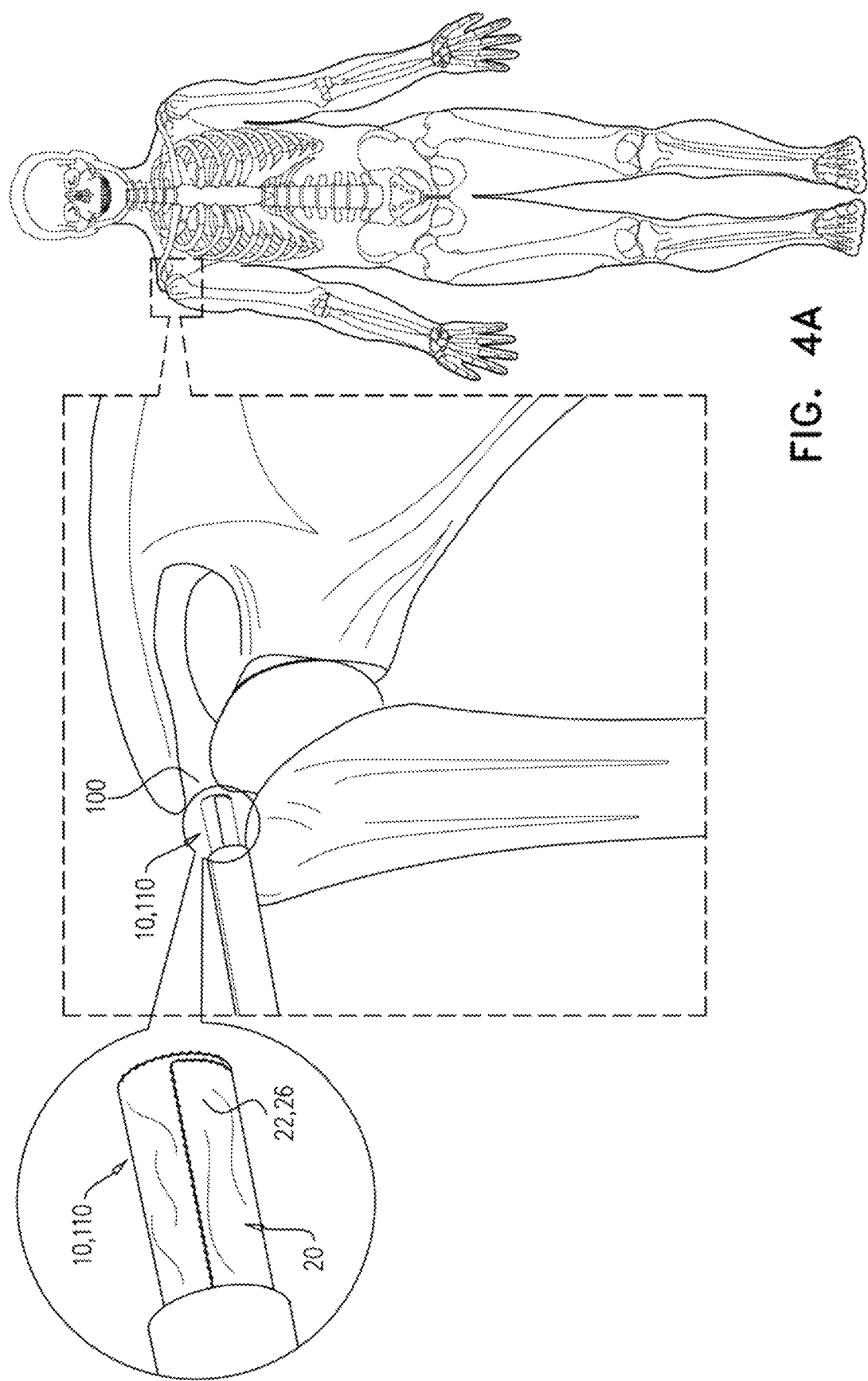

Reference is now made to FIGS. 4A-B, which are schematic illustrations of a method of deploying joint spacer 10 into a subacromial space 100 of a shoulder joint 102, in accordance with an application of the present invention. In the illustrated method, joint spacer 10 is a subacromial spacer 110, which, for example, may be used for treating a rotator cuff injury. Alternatively, joint spacer 10 is introduced into another joint and/or space (such as a knee or wrist joint), using this method mutatis mutandis.

As shown in FIG. 4A, subacromial spacer 110 is arthroscopically inserted into subacromial space 100 while pouch 20 of subacromial spacer 110 is in a compressed configuration, typically removably disposed within a delivery tube, while pouch 20 is not filled and is rolled or folded, for example.

As shown in FIG. 4B, pouch 20 is filled within shoulder joint 102, thereby transitioning pouch 20 to a filled, expanded configuration within the joint, such that subacromial spacer 110 provides mechanical support to the joint, thereby treating the joint.

For some applications, pouch 20 is filled with a volume of adipose tissue 40 within joint 102, such that subacromial spacer 110 provides the mechanical support to the joint. For some of these applications, adipose tissue 40 comprises autologous adipose tissue obtained from the subject, using techniques known in the art for obtaining autologous adipose tissue. For some applications, pouch 20 is filled with between 15 and 40 cc of adipose tissue 40.

Alternatively, subacromial spacer 110 is filled with another material, such as saline solution, autologous blood, or bone marrow.

Typically, joint spacer 10 is configured to remain intact in the joint for at least 24 months, such as at least 36 months.

For some applications, pouch 20 is configured, when filling port 28 is sealed and pouch 20 is filled to a greatest volume possible without plastic deformation of wall 22, to remain intact even upon application of an external force, by squeezing pouch 20 between two rigid planar surfaces larger than pouch 20, of 400 N, such as 500 N, 700 N, or 1000 N. Typically, pouch 20 will not remain intact upon application of an external force, by squeezing pouch 20 between two rigid planar surfaces larger than pouch 20, of 1200 N. For some applications, the maximum force that pouch 20 can withstand depends on the size of the pouch. For example, small (3×2 cm), medium (5×3.5 cm), and large (6×4 cm) pouches 20 may be able to withstand the application of a force of 500 N, 700 N, and 1000 N, respectively. (It is to be understood that the above-mentioned two rigid planar surfaces are not part of the apparatus, but are instead abstract geometric forms used to describe physical properties of pouch 20.)

Several characteristics of pouch 20 have been described and/or claimed with respect to the state of pouch 20 "when filled to a greatest volume possible without plastic deformation of wall 22." Alternatively, these characteristics may also be applicable with respect to the state of pouch 20 when filled to a greatest volume possible without elastic deformation of wall 22.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising a joint spacer for treatment of a joint of a human subject, the joint spacer comprising:
    a pouch having a wall comprising a dermal graft material; and
    a filling port for the pouch,
    wherein the joint spacer is configured to be inserted into a space of the joint, and is shaped, when the pouch is inserted into the space and filled, to provide mechanical support to the joint, and
    wherein the pouch is configured, when the filling port is sealed and the pouch is filled to a greatest volume possible without plastic deformation of the wall, to remain intact upon application of a force, by squeezing the pouch between two rigid planar surfaces larger than the pouch, of 400 N.

2. The apparatus according to claim 1, wherein the wall of the pouch does not comprise any metal or polymer.

3. The apparatus according to claim 1, wherein the wall of the pouch comprises only biological material.

4. The apparatus according to claim 1, wherein an average thickness of the wall is between 1 and 4 mm.

5. The apparatus according to claim 1, wherein the pouch, when filled to the greatest volume possible without plastic deformation of the wall, is shaped so as to define two major surfaces facing away from each other, and wherein each of the major surfaces bulges away from a plane between the two major surfaces.

6. The apparatus according to claim 5, wherein when the pouch is filled to the greatest volume possible without plastic deformation of the wall, the two major surfaces are generally symmetrical about the plane between the two major surfaces.

7. The apparatus according to claim 1, wherein the pouch, at least when not filled, is shaped so as to define two major surfaces facing away from each other, the major surfaces having respective generally rectangular perimeters.

8. The apparatus according to claim 7, wherein a ratio of longer sides to shorter sides of the generally rectangular perimeter of each of the major surfaces is between 1.25:1 and 1.75:1.

9. The apparatus according to claim 1, wherein the pouch, when filled to the greatest volume possible without plastic deformation of the wall, has a volume of between 15 and 40 cc.

10. The apparatus according to claim 1, wherein the joint spacer is a subacromial spacer and the joint is a shoulder joint, and wherein the subacromial spacer is shaped and sized so as to be insertable into a subacromial space of the shoulder joint to provide support to the shoulder joint.

11. The apparatus according to claim 1, further comprising a volume of adipose tissue suitable for filling the pouch, wherein the joint spacer is shaped, when the pouch is filled with the volume of the adipose tissue, to provide the mechanical support to the joint.

12. Apparatus comprising a joint spacer for treatment of a joint of a human subject, the joint spacer comprising:
a pouch having a wall comprising a dermal graft material, wherein the joint spacer is configured to be inserted into a space of the joint, and is shaped, when the pouch is inserted into the space and filled, to provide mechanical support to the joint,
further comprising a volume of bone marrow suitable for filling the pouch, wherein the joint spacer is shaped, when the pouch is filled with the volume of the bone marrow, to provide the mechanical support to the joint.

13. The apparatus according to claim 12, wherein the joint spacer comprises a filling port for the pouch.

14. The apparatus according to claim 13, wherein the pouch is configured, when the filling port is sealed and the pouch is filled to a greatest volume possible without plastic deformation of the wall, to remain intact upon application of a force, by squeezing the pouch between two rigid planar surfaces larger than the pouch, of 400 N.

15. The apparatus according to claim 12, wherein the pouch, when filled to a greatest volume possible without plastic deformation of the wall, has a volume of between 15 and 40 cc.

16. The apparatus according to claim 12, wherein the joint spacer is a subacromial spacer and the joint is a shoulder joint, and wherein the subacromial spacer is shaped and sized so as to be insertable into a subacromial space of the shoulder joint to provide support to the shoulder joint.

17. A method for treating a joint of a human subject, the method comprising:
inserting, into a space of the joint, a joint spacer including a pouch having a wall including a dermal graft material; and
filling, via a filling port for the pouch, the pouch within the joint, such that the joint spacer provides mechanical support to the joint,
wherein the pouch is configured, when the filling port is sealed and the pouch is filled to a greatest volume possible without plastic deformation of the wall, to remain intact upon application of a force, by squeezing the pouch between two rigid planar surfaces larger than the pouch, of 400 N.

18. A method for treating a joint of a human subject, the method comprising:
inserting, into a space of the joint, a joint spacer including a pouch having a wall including a dermal graft material; and
filling the pouch with a volume of bone marrow within the joint, such that the joint spacer provides mechanical support to the joint.

\* \* \* \* \*